United States Patent
Ye et al.

(10) Patent No.: US 10,612,325 B2
(45) Date of Patent: Apr. 7, 2020

(54) MONITORING OF THE OIL TO WATER RATIO FOR DRILLING FLUIDS

(71) Applicant: Halliburton Energy Services, Inc., Houston, TX (US)

(72) Inventors: Xiangnan Ye, Cypress, TX (US); Sorin Gabriel Teodorescu, The Woodlands, TX (US); Dale E. Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/522,839

(22) PCT Filed: Dec. 17, 2014

(86) PCT No.: PCT/US2014/070881
§ 371 (c)(1),
(2) Date: Apr. 28, 2017

(87) PCT Pub. No.: WO2016/099489
PCT Pub. Date: Jun. 23, 2016

(65) Prior Publication Data
US 2017/0321504 A1    Nov. 9, 2017

(51) Int. Cl.
| | | |
|---|---|---|
| *E21B 21/01* | (2006.01) | |
| *E21B 21/00* | (2006.01) | |
| *E21B 21/06* | (2006.01) | |
| *E21B 21/08* | (2006.01) | |

(52) U.S. Cl.
CPC ............. *E21B 21/01* (2013.01); *E21B 21/00* (2013.01); *E21B 21/06* (2013.01); *E21B 21/08* (2013.01)

(58) Field of Classification Search
CPC ........... E21B 21/01; E21B 21/06; E21B 21/08
See application file for complete search history.

(56) References Cited

U.S. PATENT DOCUMENTS 3,308,894 A * 3/1967 Reinhart ................. E21B 21/16
166/254.1
3,750,766 A * 8/1973 Thompson .............. E21B 21/08
175/48
(Continued)

FOREIGN PATENT DOCUMENTS

WO        2014110338           7/2014
WO     WO-2015105489 A1 *   7/2015  ............. E21B 47/10

OTHER PUBLICATIONS

Wikipedia Page For Relative Permittivity last modified Aug. 20, 2014 retrieved from https://en.wikipedia.org/wiki/Relative_permittivity.
(Continued)

*Primary Examiner* — James G Sayre
(74) *Attorney, Agent, or Firm* — Tenley Krueger; C. Tumey Law Group PLLC (57) ABSTRACT

Methods and systems for monitoring the oil to water ratio of a drilling fluid are disclosed. An example drilling fluid monitoring and handling system comprises a mud pit coupled to a fluid supply system and a fluid analysis system. The fluid supply system is coupled to the mud pit and the fluid analysis system. The fluid analysis system is coupled to the mud pit and the fluid supply system, wherein the fluid analysis system comprises a dielectric probe.

18 Claims, 5 Drawing Sheets

(56) References Cited

U.S. PATENT DOCUMENTS

| | | | | |
|---|---|---|---|---|
| 4,474,240 A * | 10/1984 | Oliver, Jr. | ............... | C09K 8/12 |
| | | | | 166/312 |
| 4,872,949 A | 10/1989 | Wilwerding | | |
| 4,979,393 A * | 12/1990 | Leung | ................... | E21B 49/005 |
| | | | | 324/376 |
| 6,655,221 B1 | 12/2003 | Aspelund et al. | | |
| 6,938,470 B2 | 9/2005 | DiFoggio et al. | | |
| 7,327,146 B2 * | 2/2008 | Simon | ..................... | G01V 3/30 |
| | | | | 324/324 |
| 7,363,160 B2 | 4/2008 | Seleznev et al. | | |
| 7,823,656 B1 * | 11/2010 | Williams | ................ | E21B 21/01 |
| | | | | 175/206 |
| 7,844,401 B2 | 11/2010 | Reittinger | | |
| 7,908,930 B2 | 3/2011 | Xie et al. | | |
| 7,950,472 B2 * | 5/2011 | DiFoggio | ................ | E21B 47/06 |
| | | | | 175/38 |
| 8,076,950 B2 * | 12/2011 | Wee | ................... | G01N 33/1833 |
| | | | | 324/722 |
| 8,142,634 B2 | 3/2012 | McCosh | | |
| 8,191,416 B2 | 6/2012 | Kuchuk et al. | | |
| 8,324,912 B2 | 12/2012 | Waid et al. | | |
| 8,521,436 B2 | 8/2013 | Agar et al. | | |
| 8,662,168 B2 | 3/2014 | Levy | | |
| 9,518,434 B1 * | 12/2016 | Champness | ............. | E21B 21/01 |
| 9,777,542 B2 * | 10/2017 | Stock | ..................... | E21B 21/01 |
| 2003/0132033 A1 | 7/2003 | Jones et al. | | |
| 2007/0084638 A1 * | 4/2007 | Bohnsack | ............... | E21B 21/01 |
| | | | | 175/66 |
| 2007/0169540 A1 * | 7/2007 | Sterner | .................. | E21B 21/01 |
| | | | | 73/19.09 |
| 2009/0296086 A1 | 12/2009 | Appel et al. | | |
| 2011/0203999 A1 * | 8/2011 | Simpson | ............. | B01D 25/127 |
| | | | | 210/710 |
| 2011/0251795 A1 | 10/2011 | Difoggio | | |
| 2012/0273273 A1 * | 11/2012 | Ligneul | ................ | G01N 27/221 |
| | | | | 175/46 |
| 2013/0240205 A1 | 9/2013 | Tosi | | |
| 2014/0062487 A1 | 3/2014 | Bloemenkamp | | |
| 2014/0202772 A1 | 7/2014 | Kulkarni et al. | | |

OTHER PUBLICATIONS

International Search Report and Written Opinion for Application No. PCT/US14/070881 dated Sep. 1, 2015.

Advances in Resistivity Processing Improve Well Interpretation by Frank Hearn et al., dated Mar. 15, 1999.

* cited by examiner

MONITORING OF THE OIL TO WATER RATIO FOR DRILLING FLUIDS

BACKGROUND

Provided are systems and methods for monitoring the oil to water ratio of drilling fluids. More particularly, systems and methods may be provided for a real-time analysis of shifts in the oil to water ratio of a drilling fluid that is being circulated in a wellbore.

During the drilling of a wellbore into a subterranean formation, a drilling fluid, also referred to as a drilling mud, may be continuously circulated from the surface down to the bottom of the wellbore being drilled and back to the surface again. The drilling fluid serves several functions, one of them being to transport wellbore cuttings up to the surface where they are separated from the drilling fluid. Another function of the drilling fluid is to provide hydrostatic pressure on the walls of the drilled wellbore so as to prevent wellbore collapse and the resulting influx of gas or liquid from the formations being drilled. For these and other reasons, it can be important to precisely know the characteristics and chemical composition of the drilling fluid.

Determining the oil to water ratio in a drilling fluid may be essential to an efficient drilling operation. The oil to water ratio allows operators of a drilling operation to determine the fluid rheology, the impact the drilling fluid may have on the formation, the salinity of the drilling fluid, density, filtration characteristics or requirements, etc. For example, a fluid that is too viscous may reduce drilling efficiency; conversely a fluid that is not viscous enough may be leached out to the formation and lost. A correctly formulated and maintained drilling fluid composition may be necessary to maintain the filter cake and to ensure that drill solids, such as drill cuttings, make it to the surface.

Typically, the oil to water ratio has been measured using a technique called a retort. A retort uses a distillation unit to heat and then distill the oil and water in a drilling fluid. The volume fraction of each is then compared to the original known volume used during formulation of the drilling fluid in order to measure the changes to the drilling fluid during use. This process can take an hour or more. Further, it cannot be done in real-time on the actual drilling mud while it is being circulated, as distillation of the entire fluid would be impractical, thus the process requires the use of a sample of small enough volume to be adequately distilled by the distillation unit in a practical amount of time. As such, the retort process is slower to perform and provides measurements that lag relative to the operation. The retort measurements only illustrate the oil to water ratio of the drilling fluid when the sample was taken and cannot illustrate the oil to water ratio of the drilling fluid as it is presently being circulated. This in turn may lead to delayed correction of the drilling fluid and a reduction in the overall efficiency of the operation.

BRIEF DESCRIPTION OF THE DRAWINGS

These drawings illustrate certain aspects of some examples of the present invention, and should not be used to limit or define the invention.

DETAILED DESCRIPTION

Provided are systems and methods for monitoring the oil to water ratio of drilling fluids. More particularly, systems and methods may be provided for a real-time analysis of shifts in the oil to water ratio of a drilling fluid that is being circulated in a wellbore.

As disclosed below, systems and methods may be provided for monitoring the oil to water ratio of drilling fluids. Drilling fluids may be emulsions of oil and water with various additives such as emulsifiers, viscosifiers, density modifiers, etc. One type of drilling fluid is an oil-based mud ("OBM"), where oil is the continuous phase and water, brine, or other non-miscible material is the internal phase. With any drilling fluid comprising an emulsion, the ratio of oil to water ("O/W ratio") and the amount of additives in the drilling fluid typically should be maintained in a careful balance so as to provide a strong, stable emulsion. Since oil and water, (i.e. the internal and external phases) have different capabilities of holding an electric charge, the dielectric constant of a drilling fluid may be measured and compared with a calibration curve or other known baseline to determine the O/W ratio of the drilling fluid or relative changes in the O/W ratio. Thus, the dielectric constants of drilling fluids may be standardized and the measurement of the dielectric constant of a drilling fluid may be taken in real-time and compared to this standardization to ascertain the O/W ratio of a drilling fluid. Advantageously, the systems and methods disclosed herein may allow an operator or an automated process to quickly and efficiently ascertain a drilling fluid's O/W ratio and then adjust the compositional makeup of the drilling fluid to counter changes from exposure to the formation or to anticipate changes in the formation that will occur as drilling continues. This may make it possible to improve reactivity times for drilling fluid adjustments and to monitor drilling fluid changes as they happen.

Drilling fluid monitoring and handling systems are disclosed. The drilling fluid monitoring and handling systems may comprise a mud pit coupled to a fluid supply system and a fluid analysis system; a fluid supply system coupled to the mud pit and the fluid analysis system; and a fluid analysis system coupled to the mud pit and the fluid supply system, wherein the fluid analysis system comprises a dielectric probe. The fluid analysis system may be configured to measure and analyze the dielectric constant of drilling fluid. The fluid analysis system may be configured to compute the oil to water ratio and the salinity of a drilling fluid. The fluid analysis system further may comprise at least one analysis system selected from the group consisting of an optical measuring system, an imaging measuring system, a laser measuring system, an ultrasound measuring system, a pH measuring system, density measurement system, emulsion stability system, rheology measurement system, and a titration system. The mud pit may comprise a drilling fluid. The drilling fluid may comprise a nonaqueous fluid continuous phase and an aqueous fluid internal phase. The mud pit may comprise a mixing system. The fluid supply system may comprise a pumping system. The fluid supply system may comprise at least one filter. The drilling fluid monitoring and handling system may be in fluid communication with a drilling system capable of drilling a wellbore.

Another method for monitoring the oil to water ratio of a drilling fluid is disclosed. The method comprises using a dielectric probe to measure a dielectric constant of the drilling fluid; comparing the measured dielectric constant to a predetermined dielectric constant correlated with an oil to water ratio; and selecting the oil to water ratio as the oil to water ratio of the drilling fluid. The method may further comprise adjusting the oil to water ratio of the drilling fluid in response to the selecting the oil to water ratio. The method may further comprise circulating the drilling fluid in the wellbore. The method may further comprise adding drilling fluid additives to the drilling fluid in response to the selecting the oil to water ratio.

A method for monitoring the oil to water ratio of a drilling fluid is disclosed. The method comprises placing a dielectric probe in a portion of the drilling fluid that has been recirculated; measuring the dielectric constant of the portion of the drilling fluid; and determining the oil to water-ratio of the drilling fluid based at least in part on the dielectric constant. The method may further comprise adjusting the oil to water ratio of the drilling fluid in response to the determined oil to water ratio. The method may further comprise adding drilling fluid additives to the drilling fluid in response to the determined oil to water ratio. The drilling fluid additives may be any drilling fluid additive selected from the group consisting of emulsifiers, viscosifiers, and density modifiers. The method may further comprise using a fluid reconditioning system to alter the drilling fluid. The fluid reconditioning system may comprise at least one of a shaker, a centrifuge, a hydrocyclone, a separator, a desilter, a desander, a separator, a filter, a heat exchanger, or fluid reclamation equipment.

Figure 1:
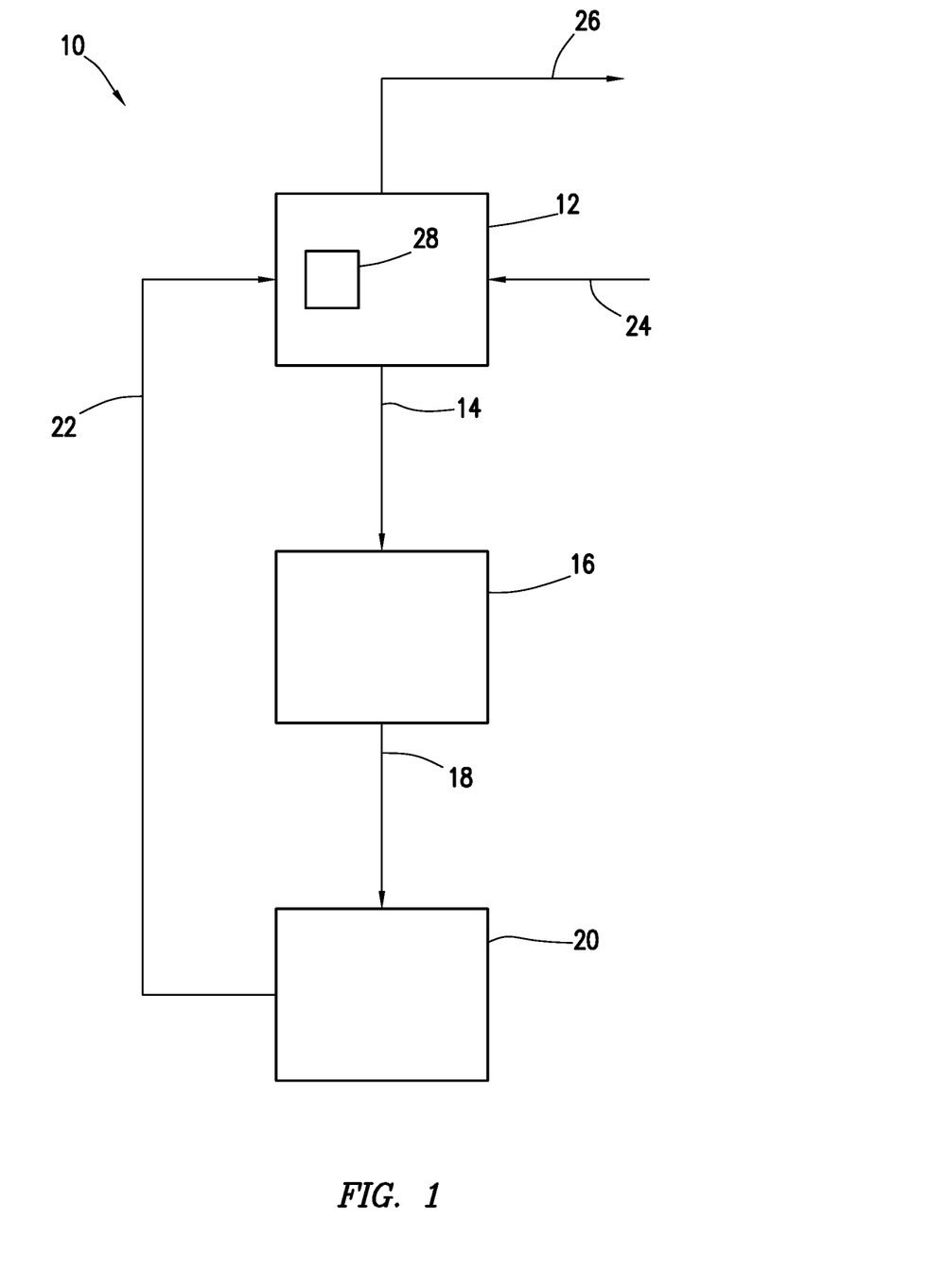
FIG. 1 illustrates an example block diagram using a fluid handling and monitoring system.

Referring now to FIG. 1, a block flow diagram is shown generally depicting an overview of the drilling fluid monitoring and handling system 10 for monitoring properties of drilling fluids such as the O/W ratio, salinity, etc. As illustrated, a portion of the drilling fluid from mud pit 12 comprising an OBM may be fed via mud pit line 14 to a fluid supply system 16. The portion of the drilling fluid may then be fed via fluid supply line 18 to a fluid analysis system 20 comprising a probe capable of measuring a dielectric constant. After fluid analysis, the portion of the drilling fluid may be returned to mud pit 12 via return line 22. Drilling fluid additives via a drilling fluid additive supply 24 may be added to mud pit 12 consistent with the analysis provided by the fluid analysis system 20. After the drilling fluid additives have been added, another portion of the drilling fluid may be retested to verify the drilling fluid was correctly formulated by transferring the drilling fluid to fluid supply 16 via mud pit line 14 or the drilling fluid may be sent to the wellbore for use in drilling fluid operations via wellbore line 26.

The drilling fluid may be any emulsion of oil and water (e.g., an OBM) in which analysis, for example, at a well site, may be desired. An oil based mud is a drilling fluid in which the continuous phase is a nonaqueous fluid and the internal phase is an aqueous fluid. Water as used herein, refers to any aqueous fluid, and more generally to any fluid that is non-miscible with the oil, and is used for the internal phase of the drilling fluid. Examples of water may include fresh water, salt water, brines or any other fluid which is non-miscible with the external or continuous phase. Oil, likewise, as used herein is used to represent any nonaqueous fluid used for the external or continuous phase of the drilling fluid. Examples of nonaqueous fluids may include hydrocarbon liquids or more generally any product obtained from oil such as diesel oil or mineral oil. Further, the term nonaqueous fluid also encompasses synthetic muds or any nonaqueous fluid that is analogous to oil muds and may be analyzed using the methods and systems described herein. The O/W ratio describes the ratio of the nonaqueous fluid to the aqueous fluid. The drilling fluid may additionally comprise drilling fluid additives, which may include viscosifiers, emulsifiers, density modifiers, etc. The drilling fluid may comprise solids. The solids may be any type of solids found in a wellbore or introduced into a wellbore fluid. Without limitation, examples of solids may include pieces of the formation, drill cuttings, and additives introduced to a drilling fluid, e.g., lost circulation materials, etc. The solids may be of any of a variety of sizes and shapes. The drilling fluid may be analyzed as described herein to determine one or more fluid properties. For example, the drilling fluid may be analyzed to determine the O/W ratio.

Mud pit 12 may be any vessel suitable for holding a drilling fluid. Drilling fluid additives may be added to mud pit 12 if desired. Mud pit 12 may comprise a container such as a drum or tank, or a series of containers that may or may not be connected. Mud pit 12 may comprise mixing equipment to mix the contents of mud pit 12 as well as any drilling fluid additives. Mud pit 12 may further comprise pumping equipment to pump the contents of mud pit 12, for example, to pump a drilling fluid to fluid supply system 16 via mud pit line 14 or to pump a drilling fluid to the wellbore via wellbore line 26.

As noted above, mud pit 12 may comprise a mixing system, illustrated in FIG. 1 as mixing system 28. Mixing system 28 may use any suitable mixing technique for mixing of the drilling fluid. While not illustrated, in the disclosed examples, mixing system 28 may also mix emulsifiers, viscosifiers, density modifying agents, and other drilling fluid additives with the drilling fluid. Further, should the O/W ratio require adjustment based on the analysis provided by fluid analysis system 20, additional nonaqueous fluid or aqueous fluid may be added to the drilling fluid in mud pit 12 and mixed by mixing system 28. Finally, mixing system 28 may more generally be used to prevent the settling of solids if desired. Mixing system 28 may use any of a variety of different mixing equipment, such as static or dynamic mixers. One example of suitable mixing equipment may comprise a vessel with a paddle wherein the paddle may be used to mixing the drilling fluid.

Fluid supply system 16 may be any type of fluid supply system used to pump a fluid. Fluid supply system 16 may pump a fluid (e.g., a drilling fluid) in a continuous or noncontinuous manner. Fluid supply system 16 may comprise filtering equipment to remove solids from the fluid. For example, the fluid supply system 16 may remove calcium carbonate and/or lost circulation materials from the fluid.

Fluid analysis system 20 may comprise at least one dielectric probe. Fluid analysis system 20 may use at least one dielectric probe to analyze a drilling fluid to determine one or more properties thereof, such as the O/W ratio, salinity, density, presence of solids, etc. Additionally, fluid analysis system 20 may measure other fluid properties using additional measurement devices and/or techniques such as optical measuring systems, imaging measuring systems, laser measuring systems, ultrasound measuring systems, pH measuring systems, density measurement system, emulsion stability system, rheology measurement system, and titration systems, among others. Combinations of fluid analysis techniques may also be used.

The dielectric probe may be any type of dielectric probe useful for measuring the dielectric constant of a drilling fluid. The dielectric probe may measure the drilling fluid by measuring frequencies in the range of about 100 Hz to about 10 MHz. If the preferred frequency of a drilling fluid is unknown, for example, if the specific compositional makeup of the fluid has never been measured or the fluid has been altered through circulation in a wellbore, the dielectric probe may sweep the available range of frequencies to find the frequency the provides the fastest response. The dielectric probe may then use this preferred frequency to measure the dielectric constant. This measurement may be compared to a calibration curve of known O/W ratios for the specific type of drilling fluid in use. From this comparison, the O/W ratio of the drilling fluid may be determined.

Figure 2:
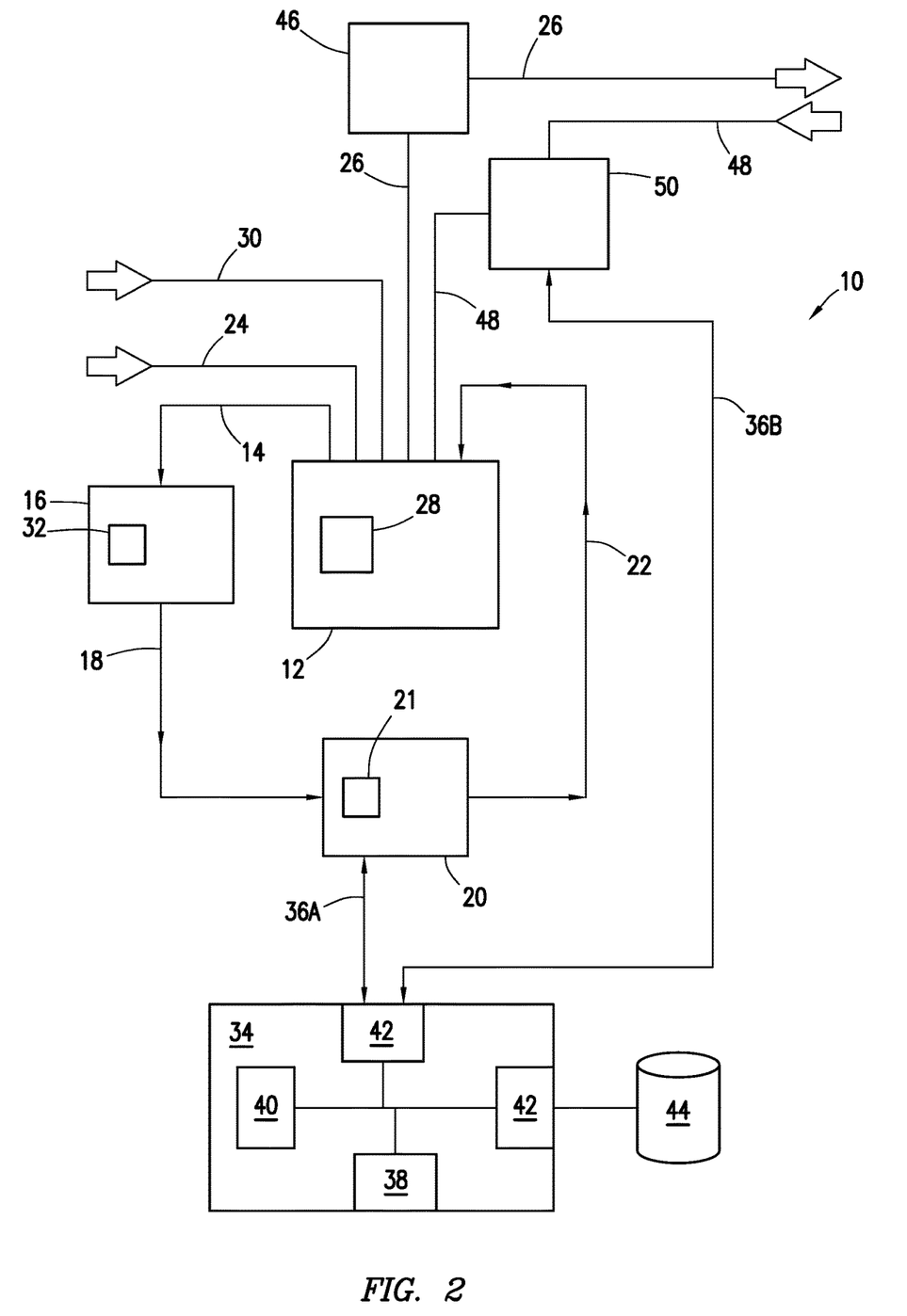
FIG. 2 illustrates an example drilling fluid handling and monitoring system using a dielectric probe to analyze the dielectric constant of a drilling fluid during a drilling operation.

Referring now to FIG. 2, an example of the fluid monitoring and handling system 10 is shown in more detail. As illustrated, the fluid monitoring and handling system 10 may comprise mud pit 12, fluid supply system 16, and fluid analysis system 20. Mud pit 12 may be supplied with a drilling fluid from an initial drilling fluid supply line 30 or return line 22. Drilling fluid supply line 30 provides an initial supply of drilling fluid to mud pit 12. The initial supply of drilling fluid does not imply that the drilling fluid has not been recycled or circulated in the wellbore, but simply indicates that this supply is not presently being circulated or otherwise used in the wellbore. A mud-mixing hopper (not shown) may be coupled to initial drilling fluid supply line 30 and used to mix a new drilling fluid before the drilling fluid is sent to the mud pit. Return line 22 returns circulated drilling fluid to mud pit 12. As discussed above, mud pit 12 may comprise mixing system 28 which may be used to mix the drilling fluid with drilling fluid from initial drilling fluid supply line 30, return line 22, drilling fluid additives, additional nonaqueous fluid, aqueous fluid, or more generally to prevent solids within the drilling fluid from settling. Mixing system 28 may comprise a static mixer, dynamic mixer, of other suitable mixer.

As described above, mud pit line 14 conveys a portion of the drilling fluid to the fluid supply system 16 where the portion of the drilling fluid may be conditioned and solids may be removed. Mud pit line 14 may be a suction line, and as such would pull the portion of the drilling fluid from mud pit 12 to fluid supply system 16. Fluid supply system 16 may comprise at least one fluid supply pumping system 32. The pump may be any type of pump suitable for pumping the portion of the drilling fluid to the fluid analysis system including a mud pump or analogous pump and/or pumping system. The fluid supply system 16 may then pump the drilling fluid to the fluid analysis system 20 via fluid supply 18.

Fluid analysis system 20 may analyze the portion of the drilling fluid in a continuous or noncontinuous manner as desired based on whether flow through fluid analysis system 20 is continuous or noncontinuous. As described above, fluid analysis system may comprise a dielectric probe 21. Optionally, fluid analysis system 20 may analyze the portion of the drilling fluid at a standard pressure and temperature to provide consistent measurements and to also minimize gas bubbles. Using the dielectric probe 21 as described above, the fluid analysis system 20 may measure the dielectric constant of the portion of the drilling fluid and record the results. The dielectric constant measurement, recordation, and analysis process may be automated in part or in whole. Alternatively, the process may not be automated. Further the process may provide feedback for the adjustment of one or more components of the fluid monitoring and handling system 10. For example, the results of the analysis performed by the fluid analysis system 20 may indicate that adjustment should be made at an upstream or downstream process within or external to the fluid monitoring and handling system 10 as discussed below. Such adjustment may be automated in part or in whole. Alternatively, said adjustment may not be automated.

The analysis of the dielectric constant made by the dielectric probe 21 may comprise using the dielectric probe 21 to measure the response the dielectric constant of the portion of the drilling fluid. The configuration may comprise installation of an access tube in a location where a portion of the drilling fluid may pass over it. Alternatively, the dielectric probe 21 may also be modular. The sensing portion consists of an oscillator circuit, the frequency is determined by an annular electrode, fringe-effect capacitor, and the dielectric constant of the portion of the drilling fluid. Each capacitor sensor consists of two metal rings mounted on the circuit board at some distance from the top of the access tube. These rings are a pair of electrodes, which form the plates of the capacitor with the portion of the drilling fluid acting as the dielectric in between. The plates are connected to an oscillator, consisting of an inductor and a capacitor. The oscillating electrical field may be generated between the two rings and may extend into the portion of the drilling fluid. The capacitor and the oscillator form a circuit, and changes in dielectric constant of surrounding media are detected by changes in the operating frequency. The dielectric probe may comprise two parallel plates with a known gap and area. Alternatively, the dielectric probe may comprise two coaxial cylinders. The output of the dielectric probe 21 is the frequency response of the portion of the drilling fluid's capacitance due to its O/W ratio.

The examples disclosed herein contemplate the placement of the dielectric probe 21 at any point in the fluid monitoring and handling system 10. For example, one or more dielectric probes 21 may be placed in the fluid analysis system 20, the fluid reconditioning system 50 (discussed below), the mud pit 12, as well as within the wellbore or in an exit conduit from the wellbore. As such, all examples disclosed herein contemplate the measuring of the dielectric constant at any point in the drilling fluid handling process, so that the drilling fluid may be monitored and/or subsequently adjusted as desired.

Figure 3:
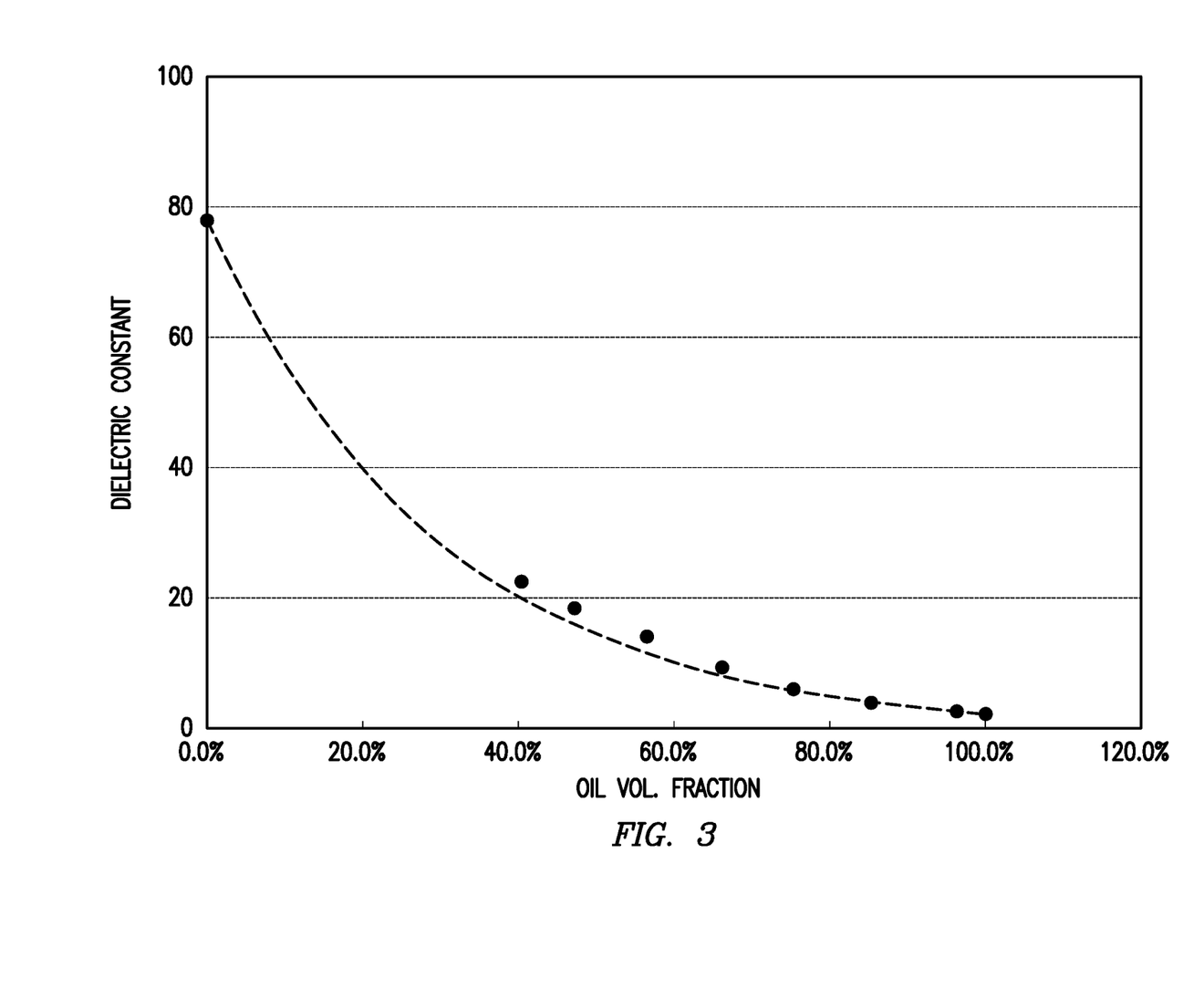
FIG. 3 illustrates an example calibration curve for the measurement of the oil to water ratio of a drilling fluid.

The measurement of the dielectric constant may be recorded and compared to a calibration curve. The calibration curve may comprise plotted data points obtained from measuring the dielectric constant for a specific formulation of a drilling fluid in which the O/W ratio was varied at desired intervals. A curve may then be fit to these data points. A measured dielectric constant for a matching drilling fluid formulation may be compared to this calibration curve to find the corresponding O/W ratio. FIG. 3 illustrates an example calibration curve fitted with an exponential function of $Y=78e^{-3.428X}$. The measurement of the dielectric constant may also be used to analyze the salinity, presence of solids, and the like.

The analysis performed by fluid analysis system 20 may be performed by computer system 34. Computer system 34 may be an internal or external component of fluid analysis system 20. FIG. 2 illustrates computer system 34 as an external component of fluid analysis system 20. Computer system 34 is connected to fluid analysis system via communication link 36A. Communication link 36A may include a direct connection, a private network, a virtual private network, a local area network, a WAN (e.g., an Internet-based communication system), a wireless communication system (e.g., a satellite communication system, telephones), combinations thereof, or any other suitable communication link. Computer system 34 may be any suitable data processing system, including computer systems, handheld devices, or any other suitable device. A suitable data processing system may include processor 38, memory 40, and software operable on processor 38 to process and analyze the measurement data generated by fluid analysis system 20, adjust the parameters of fluid monitoring and handling system 10, and/or operate a part or the whole of fluid monitoring and handling system 10. Computer system 34 may comprise a processor 38, memory 40, and input/output ("I/O") interface(s) 42. Processor 38 may comprise one central processing unit or may be distributed across one or more processors in one or more locations. Memory 40 should be communicatively coupled to processor 38. Memory 40 may be read-only memory, random-access memory, or the like. I/O interface(s) 42 should be communicatively coupled to processor 38. I/O interface(s) 42 may be any suitable system for connecting computer system 34 to a communication link, such as a direct connection, a private network, a virtual private network, a local area network, a wide area network ("WAN"), a wireless communication system, or combinations thereof; storage devices, such as storage 44; external devices, such as a keyboard, a monitor, a printer, a voice recognition device, or a mouse; or any other suitable system. Optionally, storage 44 may also be provided. Storage 44 may be communicatively coupled to I/O interface(s) 42 or to processor 38. Storage 44 may comprise any device suitable for storing data to be processed, including, but not limited to, compact disc drives, floppy drives, hard disks, flash memory, solid state drives, and the like. Those of ordinary skill in the art will appreciate that suitable data processing systems may comprise additional, fewer, and/or different components than those described for computer system 34.

Data processing and analysis software native to fluid analysis system 20 and/or installed on computer system 34 may be used to analyze the data generated by fluid analysis system 20. This procedure may be automated such that the analysis happens without the need for operator input or control. Further, the operator may select from several previously input parameters or may be able to recall previously measured data. Any of the data may be transferable and/or storable on a USB drive if desired.

Return line 22 may return the portion of the drilling fluid to mud pit 12 from fluid analysis system 20. Drilling fluid additives may be added to mud pit 12 via drilling fluid additive supply line 24 based on the analysis of fluid analysis system 20. Should the drilling fluid require further analysis it may be further analyzed. Alternatively, portions of the drilling fluid may be continuously analyzed and returned to mud pit 12 in a continuous process with drilling fluid additives and/or water or oil added to maintain the strong and stable emulsion that the drilling fluid may have been originally formulated for. Similarly, measurements made within the wellbore may provide information as to formation features (e.g., a salt stream) that the drilling fluid may interact with as a drilling operation continues. If said information is known, the drilling fluid may be formulated to anticipate said formation features. Fluid analysis system 20 may be used to validate that the correct anticipatory formulation has been achieved prior to pumping the drilling fluid into the wellbore and the aforementioned subject formation feature.

With continued reference to FIG. 2, if a drilling fluid is of a satisfactory formulation, the drilling fluid may be pumped via wellbore line 26, which may be a suction line, to mud pump 46 which may pump the drilling fluid into the wellbore (not shown). Mud pump 46 may be any type of pump or pumping system useful for circulating a drilling fluid into a subterranean formation under a sufficient pressure. Drilling fluid that has been circulated within the wellbore, may be returned to mud pit 12 via circulated drilling fluid return line 48. Fluid reconditioning system 50 may be conducted to condition the drilling fluid prior to returning the drilling fluid to mud pit 12. Such processes may include, but are not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid reconditioning system 50 may further include one or more sensors, gauges, pumps, compressors, and the like used store, monitor, regulate, and/or recondition the drilling fluid and various additives thereto. After the drilling fluid has been reconditioned, the drilling fluid may be returned to mud pit 12 via circulated drilling fluid return line 48. Communication link 36B may link fluid reconditioning system 50 to computer system 34. Communication link 36B may include a direct connection, a private network, a virtual private network, a local area network, a WAN (e.g., an Internet-based communication system), a wireless communication system (e.g., a satellite communication system, telephones), combinations thereof, or any other suitable communication link. Communication link 36B may allow computer system 34 to adjust the parameters of fluid reconditioning system 50 based on the measurement of the dielectric constant by fluid analysis system 20. Further, fluid analysis system 20 may be used to adjust the amount of and type of additives used and supplied via drilling fluid additive supply 24. This process may be conducted via a separate communication link with the vessel or vessels in which the drilling fluid additives may be stored (not shown). Additionally, fluid analysis system 20 may be used to adjust the ratio of oil and water in any such drilling fluid supplied via initial drilling fluid supply line 28 should a new or uncirculated supply of drilling fluid be required.

Figure 4:
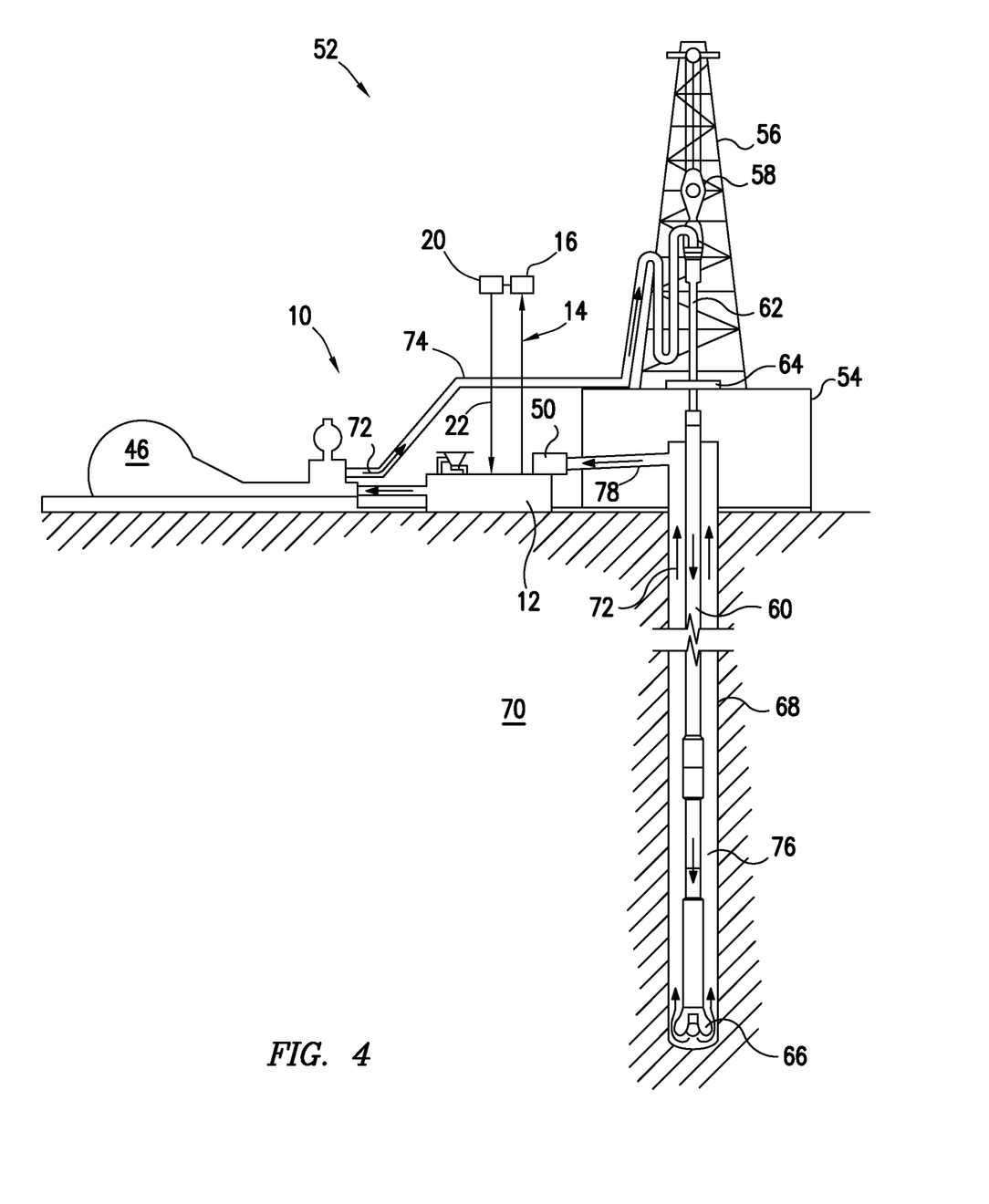
FIG. 4 illustrates an example drilling fluid system using a drilling fluid handling and monitoring system.

Referring now to FIG. 4, the disclosed fluid monitoring and handling system 10 may be used in conjunction with a drilling system 52. It should be noted that while FIG. 4 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 52 may include a drilling platform 54 that supports a derrick 56 having a traveling block 58 for raising and lowering a drill string 60. The drill string 60 may include, but is not limited to, drill pipe and coiled tubing, as generally known to those skilled in the art. A kelly 62 may support the drill string 60 as it may be lowered through a rotary table 64. A drill bit 66 may be attached to the distal end of the drill string 60 and may be driven either by a downhole motor and/or via rotation of the drill string 60 from the well surface. Without limitation, the drill bit 66 may include, roller cone bits, PDC bits, natural diamond bits, any hole openers, reamers, coring bits, and the like. As the drill bit 66 rotates, it may create a borehole 68 that penetrates various subterranean formations 70.

The drilling system 52 may further include a fluid monitoring and handling system 10 comprising component parts such as mud pump 46, one or more fluid reconditioning systems 50, and a mud pit 12. The mud pump 46 representatively includes any conduits, pipelines, trucks, tubulars, and/or pipes used to fluidically convey the drilling fluid 72 downhole, any pumps, compressors, or motors (e.g., topside or downhole) used to drive the drilling fluid 72 into motion, any valves or related joints used to regulate the pressure or flow rate of the drilling fluid 72, and any sensors (e.g., pressure, temperature, flow rate, etc.), gauges, and/or combinations thereof, and the like.

The mud pump 46 may circulate drilling fluid 72 through a feed pipe 74 and to the kelly 62, which may convey the drilling fluid 72 downhole through the interior of the drill string 60 and through one or more orifices in the drill bit 66. The drilling fluid 72 may then be circulated back to the surface via an annulus 76 defined between the drill string 60 and the walls of the borehole 68. At the surface, the recirculated or spend drilling fluid 72 may be conveyed to the fluid reconditioning system 50 via an interconnecting flow line 78. After passing through the fluid reconditioning system 50, a "cleaned" drilling fluid 72 may be deposited into a nearby mud pit 12. While illustrated as being arranged at the outlet of the wellbore 68 via the annulus 76, those skilled in the art will readily appreciate that the fluid reconditioning system 50 may be arranged at any other location in the drilling system 52 to facilitate its proper function, without departing from the scope of the scope of the disclosure.

Referring still to FIG. 4, the fluid monitoring and handling system 10 may further include a fluid supply system 16 and fluid analysis system 20, which may be disposed on a skid supported on the platform 54. The fluid analysis system 20 may, for example, continuously or intermittently measure the dielectric constant of drilling fluid 72. As illustrated, drilling fluid 72 may be taken from the mud pit 12 via a mud pit line 14 and an analyzed drilling fluid may be returned to the mud pit 12 via return line 22. Alternatively, the dielectric constant of the drilling fluid may be measured, recorded, and/or analyzed at fluid reconditioning system 50 or even while in the wellbore if desired.

EXAMPLES

To facilitate a better understanding of the present claims, the following examples of certain aspects of the disclosure are given. In no way should the following examples be read to limit, or define, the entire scope of the claims.

Example 1

Figure 5:
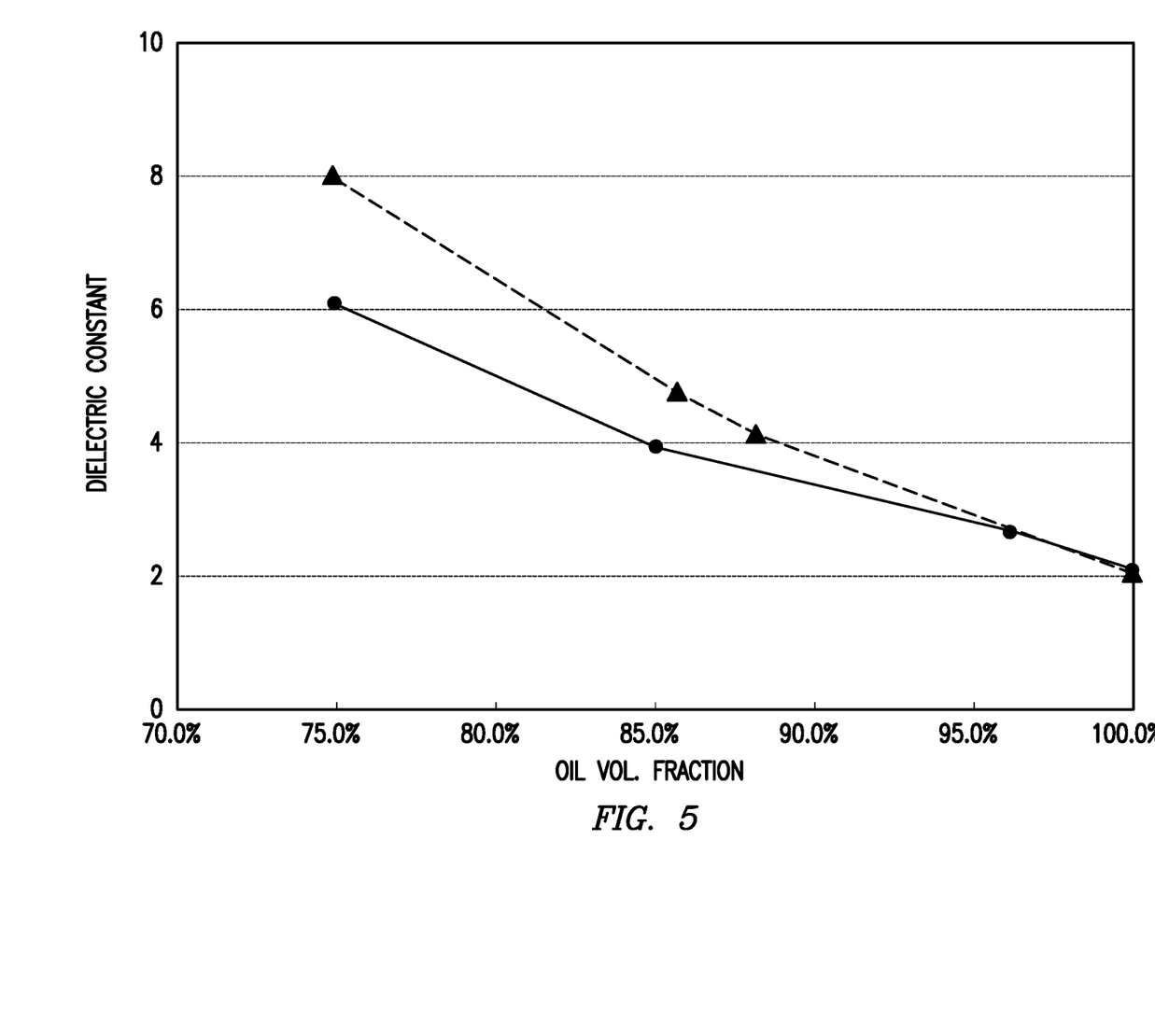
FIG. 5 illustrates an example plot depicting the measured change in the dielectric constant attributable to the use of a brine in a drilling fluid.

Example 1 illustrates that the measurement of the dielectric constant may allow for the detection of varying salinity levels as well as the measurement of said varying salinity levels. FIG. 5 illustrates a plot depicting two drilling fluid formulations with shifting O/W ratios. In the formulation represented by the solid line, deionized water was used. In the formulation represented by the dashed line, a brine comprising 250,000 ppm $CaCl_2$ was used. The formulations are otherwise the same. As shown by FIG. 5, the presence of a salt in the formulation may shift the dielectric constant relative to the same formulation without said salt. This effect allows for a measurement of the salinity of a drilling fluid. Further, the presence of solids in the drilling fluid that induce a shift in the dielectric constant may also be detected in an analogous manner.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A drilling fluid monitoring and handling system comprising:
   a mud pit including a mixing system;
   a fluid analysis system in fluid communication with the mud pit;
   a fluid supply system in fluid communication with the mud pit and the fluid analysis system and wherein the fluid supply system is configured to move a fluid from the mud pit to the fluid analysis system;
   a dielectric probe disposed within the fluid analysis system;
   a fluid reconditioning system connected to the mud pit and configured to condition a drilling fluid disposed in the mud pit;
   a fluid additive supply in fluid communication with the mud pit and configured to add an emulsifier, a viscosifier, or a density modifier to the mud pit; and a computer system, wherein the computer system is in communication with the dielectric probe and the fluid reconditioning system, wherein the computer system controls the fluid reconditioning system and an amount of the emulsifier, the viscosifier, or the density modifier added to the mud pit by the fluid additive supply based at least in part on one or more readings from the dielectric probe.

2. A system according to claim 1, wherein the fluid analysis system is configured to measure and analyze the dielectric constant of drilling fluid.

3. A system according to claim 1, wherein the fluid analysis system is configured to compute the oil to water ratio and the salinity of a drilling fluid.

4. A system according to claim 1 , wherein the fluid analysis system further comprises at least one analysis system selected from the group consisting of an optical measuring system, an imaging measuring system, a laser measuring system, an ultrasound measuring system, a pH measuring system, density measurement system, emulsion stability system, rheology measurement system, and a titration system.

5. A system according to claim 1, wherein the mud pit comprises a drilling fluid.

6. A system according to claim 5, wherein the drilling fluid comprises a nonaqueous fluid continuous phase and an aqueous fluid internal phase.

7. A system according to claim 1, wherein the fluid supply system comprises a pumping system.

8. A system according to claim 1, wherein the fluid supply system comprises at least one filter.

9. A system according to claim 1, wherein the drilling fluid monitoring and handling system is in fluid communication with a drilling system capable of drilling a wellbore.

10. A method for monitoring the oil to water ratio of a drilling fluid comprising:
moving a fluid from a mud pit to a drilling fluid analysis system with a fluid supply system;
placing a dielectric probe in at least a portion of the drilling fluid that has been circulated to the fluid analysis system with the fluid supply system from the mud pit;
measuring the dielectric constant of the portion of the drilling fluid within the dielectric probe;
sending measurements from the dielectric probe to a computer system;
determining the oil to water ratio of the drilling fluid based at least in part on the dielectric constant with the computer system;
operating a fluid additive supply with the computer system to add an emulsifier, a viscosifier, or a density modifier to the mud pit based at least in part on the dielectric constant measured by the dielectric probe; and
operating a fluid reconditioning system with the computer system to alter the drilling fluid based at least in part on the dielectric constant measured by the dielectric probe.

11. A method according to claim 10, further comprising adjusting the oil to water ratio of the drilling fluid in response to the determined oil to water ratio.

12. A method according to claim 10, further comprising adding drilling fluid additives to the drilling fluid in response to the determined oil to water ratio.

13. A method according to claim 12, wherein the drilling fluid additives may be any drilling fluid additive selected from the group consisting of emulsifiers, viscosifiers, and density modifiers.

14. A method according to claim 10, wherein the fluid reconditioning system comprises at least one of a shaker, a centrifuge, a hydrocyclone, a separator, a desilter, a desander, a separator, a filter, a heat exchanger, or fluid reclamation equipment.

15. A method for monitoring the oil to water ratio of a drilling fluid comprising:
using a dielectric probe to measure a dielectric constant of the drilling fluid within a fluid analysis system which is in fluid communication with a mud pit and wherein the drilling fluid is moved from the mud pit to the fluid analysis system by a fluid supply system;
comparing the measured dielectric constant to a predetermined dielectric constant correlated with an oil to water ratio;
selecting the oil to water ratio as the oil to water ratio of the drilling fluid;
operating a fluid additive supply with the computer system to add an emulsifier, a viscosifier, or a density modifier to the mud pit based at least in part on the dielectric constant measured by the dielectric probe; and
altering the drilling fluid with a fluid reconditioning system controlled by a computer system which is connected to the dielectric probe.

16. A method according to claim 15, further comprising adjusting the oil to water ratio of the drilling fluid in response to the selecting the oil to water ratio.

17. A method according to claim 15, further comprising circulating the drilling fluid in the wellbore.

18. A method according to claim 15, further comprising adding drilling fluid additives to the drilling fluid in response to the selecting the oil to water ratio.

* * * * *